US009648861B2

(12) United States Patent
Schmitz (10) Patent No.: US 9,648,861 B2
(45) Date of Patent: May 16, 2017

(54) DEVICE FOR KILLING BED BUGS (71) Applicant: Jack D. Schmitz, Vista, CA (US)

(72) Inventor: Jack D. Schmitz, Vista, CA (US)

( * ) Notice: Subject to any disclaimer, the term of this patent is extended or adjusted under 35 U.S.C. 154(b) by 684 days.

(21) Appl. No.: 14/033,236

(22) Filed: Sep. 20, 2013

(65) Prior Publication Data

US 2015/0082688 A1  Mar. 26, 2015

(51) Int. Cl.
*A01M 1/20* (2006.01)
*A01M 1/22* (2006.01)
*A61L 2/10* (2006.01)
*A61L 9/20* (2006.01)

(52) U.S. Cl.
CPC .......... *A01M 1/226* (2013.01); *A01M 1/2094* (2013.01); *A61L 2/10* (2013.01); *A61L 9/20* (2013.01)

(58) Field of Classification Search
CPC ........ A01M 1/20; A01M 1/2094; A01M 1/22; A01M 1/226; A01M 17/00; A01M 17/06; A01M 17/08; A61L 2/10; A61L 9/20; B65B 55/08; C02F 1/32; C02F 1/325; C92F 1/32; C92F 1/325
USPC ...................... 43/123, 132.1, 124; 422/24, 22
See application file for complete search history.

(56) References Cited

U.S. PATENT DOCUMENTS

| | | | | | |
|---|---|---|---|---|---|
| 2,223,813 | A | * | 12/1940 | Brown | A01M 1/226 422/22 |
| 2,575,426 | A | * | 11/1951 | Parnell | A23B 7/0053 34/418 |
| 3,433,947 | A | * | 3/1969 | Cram | B29C 35/08 250/442.11 |
| 4,336,279 | A | * | 6/1982 | Metzger | B29C 35/06 34/266 |
| 4,337,592 | A | * | 7/1982 | Hasegawa | A01M 1/226 43/132.1 |
| 5,364,645 | A | * | 11/1994 | Lagunas-Solar | A23L 3/28 426/248 |
| 5,607,711 | A | * | 3/1997 | Lagunas-Solar | A01M 1/226 426/248 |
| 5,680,712 | A | * | 10/1997 | Kiyokawa | F26B 3/283 34/196 |
| 6,323,462 | B1 | * | 11/2001 | Strand | F27B 9/029 34/224 |
| 6,737,029 | B2 | * | 5/2004 | Miller | A61L 2/202 422/186.07 |

(Continued)

FOREIGN PATENT DOCUMENTS

DE   4442702 A1 * 6/1996 ......... A47L 15/0002
JP   3814358 B2 * 8/2006

(Continued)

*Primary Examiner* — Darren W Ark
(74) *Attorney, Agent, or Firm* — Raymond Sun (57) ABSTRACT

A system for killing bed bugs located on the exterior crevices of an item includes a housing divided into an upper housing area and a lower housing area, front and rear flap covering apertures located in the front and rear, respectively, of the upper housing area, a horizontally disposed motorized conveyor that is located within the upper housing area, at least one heating element located in the upper housing area, two or more UV lamps located in the upper housing area, and a fan located in the upper housing area. The heating elements, one of the UV lamps, and the fan are located below the conveyor.

10 Claims, 6 Drawing Sheets

(56) References Cited

U.S. PATENT DOCUMENTS

| | | | | |
|---|---|---|---|---|
| 6,833,551 B2* | 12/2004 | Avnery | | G21K 5/10 250/492.1 |
| 6,928,143 B2* | 8/2005 | Menear | | G21K 5/10 250/453.11 |
| 7,067,089 B2* | 6/2006 | Wen | | A61L 2/10 422/28 |
| 7,294,318 B1* | 11/2007 | Miller | | A61L 2/10 422/1 |
| 7,452,561 B2* | 11/2008 | Newman | | A23B 7/015 426/248 |
| 8,389,965 B2* | 3/2013 | Kang | | A01M 1/226 144/335 |
| 8,834,788 B2* | 9/2014 | Fogg | | A61L 2/10 422/24 |
| 9,010,017 B2* | 4/2015 | Southard | | A01M 1/2094 43/132.1 |
| 9,101,125 B2* | 8/2015 | Knote | | A01M 1/2094 |
| 9,198,990 B2* | 12/2015 | Fletcher | | A61L 2/10 |
| 9,226,489 B2* | 1/2016 | Pattison | | A01M 1/2094 |
| 9,265,241 B2* | 2/2016 | Raud | | A01M 1/2094 |
| 2003/0145664 A1* | 8/2003 | Schwarz | | B07C 1/00 73/863.22 |
| 2003/0174810 A1* | 9/2003 | Korenev | | A61L 2/082 378/69 |
| 2003/0201401 A1* | 10/2003 | Rose | | G21K 5/10 250/492.1 |
| 2004/0028553 A1* | 2/2004 | Panico | | A61L 2/10 422/24 |
| 2005/0108920 A1* | 5/2005 | Takenoshita | | A01M 17/008 43/132.1 |
| 2005/0276720 A1* | 12/2005 | Correa | | A61L 9/20 422/24 |
| 2008/0178412 A1* | 7/2008 | Kiter | | A61L 2/10 15/309.2 |
| 2008/0253941 A1* | 10/2008 | Wichers | | A61L 2/10 422/186.3 |
| 2009/0211148 A1* | 8/2009 | McCarty | | A01M 1/2094 43/124 |
| 2011/0308139 A1* | 12/2011 | James | | A01M 1/2094 43/132.1 |
| 2012/0121458 A1* | 5/2012 | Tarifi | | A01M 1/226 422/24 |
| 2012/0192479 A1* | 8/2012 | Schmitz | | A01M 1/2094 43/132.1 |
| 2012/0246965 A1* | 10/2012 | Zhong | | C02F 11/12 34/386 |
| 2012/0248332 A1* | 10/2012 | Kreitenberg | | A61L 2/10 250/455.11 |
| 2012/0317870 A1* | 12/2012 | Pratt | | A01M 1/2094 43/132.1 |
| 2013/0044997 A1* | 2/2013 | French | | A01M 1/226 392/360 |
| 2013/0181141 A1* | 7/2013 | Brueck | | A61L 2/10 250/432 R |
| 2013/0269239 A1* | 10/2013 | Whitley | | A01M 1/2094 43/132.1 |
| 2014/0000648 A1* | 1/2014 | Ingle | | A61L 2/10 134/1 |
| 2015/0000185 A1* | 1/2015 | Pratt | | A01M 1/2094 43/132.1 |
| 2015/0052800 A1* | 2/2015 | Timbrook, Jr. | | A01M 1/2094 43/132.1 |
| 2015/0113856 A1* | 4/2015 | Kawashima | | A01M 1/2094 43/132.1 |
| 2015/0128483 A1* | 5/2015 | Krupp | | A01M 1/2094 43/132.1 |
| 2015/0181857 A1* | 7/2015 | Mladek | | A01M 1/2094 43/132.1 |
| 2015/0181858 A1* | 7/2015 | Southard | | A01M 1/2094 43/140 |
| 2015/0376831 A1* | 12/2015 | Ingle | | A61L 2/10 8/137 |
| 2016/0073623 A1* | 3/2016 | Pattison | | A01M 1/2094 43/132.1 |
| 2016/0074546 A1* | 3/2016 | Rizzone | | A61L 2/10 250/455.11 |

FOREIGN PATENT DOCUMENTS

| | | | | |
|---|---|---|---|---|
| KR | 20080086083 A | * | 9/2008 | |
| KR | 20140013609 A | * | 2/2014 | |
| SG | WO 2010044748 A1 | * | 4/2010 | A61L 2/10 |
| WO | WO 0185222 A1 | * | 11/2001 | A61L 2/10 |
| WO | WO 2004064874 A2 | * | 8/2004 | A61L 2/10 |

* cited by examiner

DEVICE FOR KILLING BED BUGS

BACKGROUND OF THE INVENTION

1. Field of the Invention

The present invention relates to the field of pest killing devices, and more specifically, to a heated enclosure for killing bed bugs harbored on the outside of luggage or other items.

2. Description of the Related Art

Bed bugs have been making a re-appearance in recent years as a pest species that can inhabit bedding and bite people as they sleep. Sometimes these bugs find their way from the bedding or wherever luggage is stored and crawl onto luggage where they can hide in the external crevices and overlapping flaps of luggage. Bed bugs can then crawl from one luggage item to another while carried in an airplane cargo hold, or cab, or shuttle or any other location where luggage is stored.

It is known that beg bugs, from nymph to adult, cannot withstand temperatures over 120 degrees F. It is also known that UV radiation kills germs. It would therefore be in a person's best interest to heat a luggage item to the desired kill temperature, and to treat the outer surface with UV light so that the bed bugs and other germs or bacteria will not be accidentally brought from one environment to another. For example, this can be done from a home environment to a hotel room or vice versa. There have been numerous specialty heating ovens designed for various purposes. For example W Metzger's U.S. Pat. No. 4,336,279 for curing coated substrates, or S Kiwokawa's U.S. Pat. No. 5,680,712 for drying objects.

However, no one to date has designed a heated enclosure specifically designed to hold a plurality of luggage items, and to evenly heat those luggage items for a pre-selected time and temperature for the purpose of killing bed bugs.

SUMMARY OF THE INVENTION

The primary object of the present invention is to provide a heated enclosure that is heated to approximately 160 degrees F., thereby allowing luggage stored within the enclosure to be heated to approximately 120 degrees F. and remains in the housing for approximately ninety seconds, and to then automatically send the luggage out of the heated enclosure.

Another object of the present invention is to provide a heated enclosure that can removably retain a plurality of suitcases and other luggage items via a conveyor system.

Another object of the present invention is to provide a heated enclosure that uses one or more heat sources to produce the most effective heat for killing bed bugs.

A further object of the present invention is to provide a heated enclosure that uses one or more fans to circulate air in the enclosure and to warm it and deliver air evenly throughout the enclosure.

Yet another object of the present invention is to provide a heated enclosure that also includes one or more UV light sources to kill germs and bacteria on the surface of the luggage.

Still yet another object of the present invention is to provide a heated enclosure that includes insulated front and rear flaps to reduce the loss of heat during operation.

Another object of the present invention is to provide a heated enclosure that includes a timer to automatically draw in the luggage items into the housing for approximately ninety seconds, and then to cause the luggage to exit the housing.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a system for killing bed bugs located on the exterior crevices of an item. The system includes a housing divided into an upper housing area and a lower housing area, front and rear flap covering apertures located in the front and rear, respectively, of the upper housing area, a horizontally disposed motorized conveyor that is located within the upper housing area, at least one heating element located in the upper housing area, two or more UV lamps located in the upper housing area, and a fan located in the upper housing area. The heating elements, one of the UV lamps, and the fan are located below the conveyor. A timing circuit is located in the lower housing area, the timing circuit causing the motorized conveyor to draw in one or more items through the front aperture and into the upper housing area, to retain the item within the upper housing area for a predetermined period of time, and then to deliver the item out of the upper housing area via the rear aperture.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Even though the present invention has been described in connection with killing bed bugs on luggage items, the principles of the present invention are equally applicable to any item or container which may be infested by, or attracted to, bed bugs.

Figure 1:
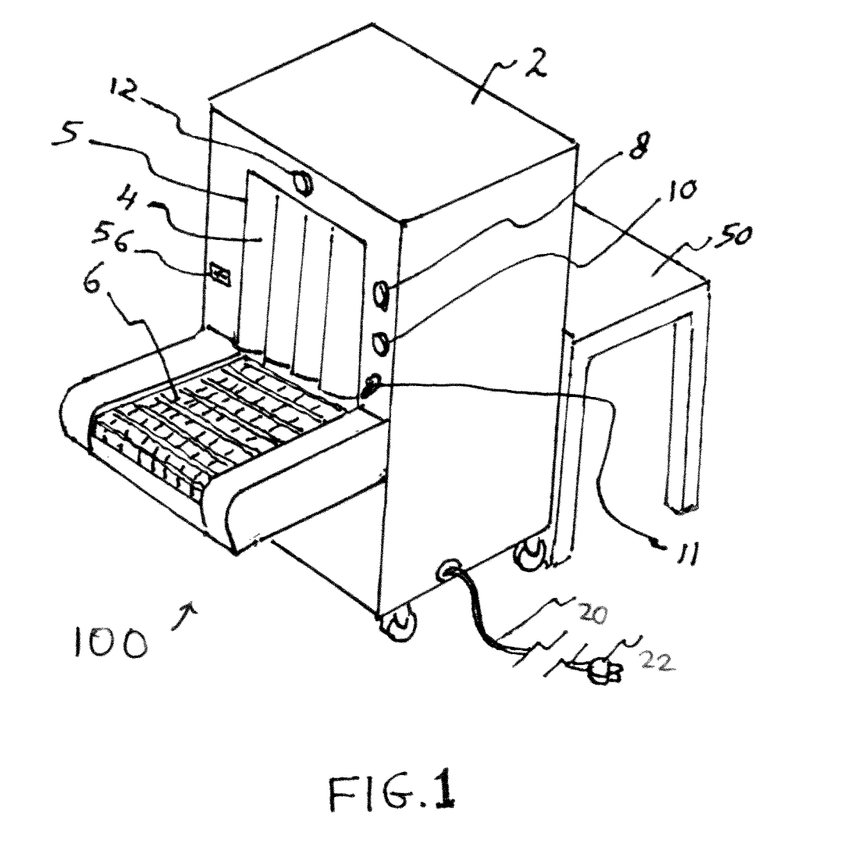
FIG. 1 is a perspective view of the present invention.

Referring now to FIG. 1, we see a perspective view of the system 100 for the present invention. A stainless steel wire mesh conveyor 6 extends from the front of a housing 2. Housing 2 includes an upper housing area 52 and a lower housing area 54 separated by partition 37 (see FIG. 5). A front aperture 5 acts as the entrance for upper housing area 52 and is covered by flexible flaps 4. In the preferred embodiment, the flexible straps are lead lined. A similar cover 22 is used to close the rear aperture 23 as shown in the front section view in FIG. 4.

Figure 4:
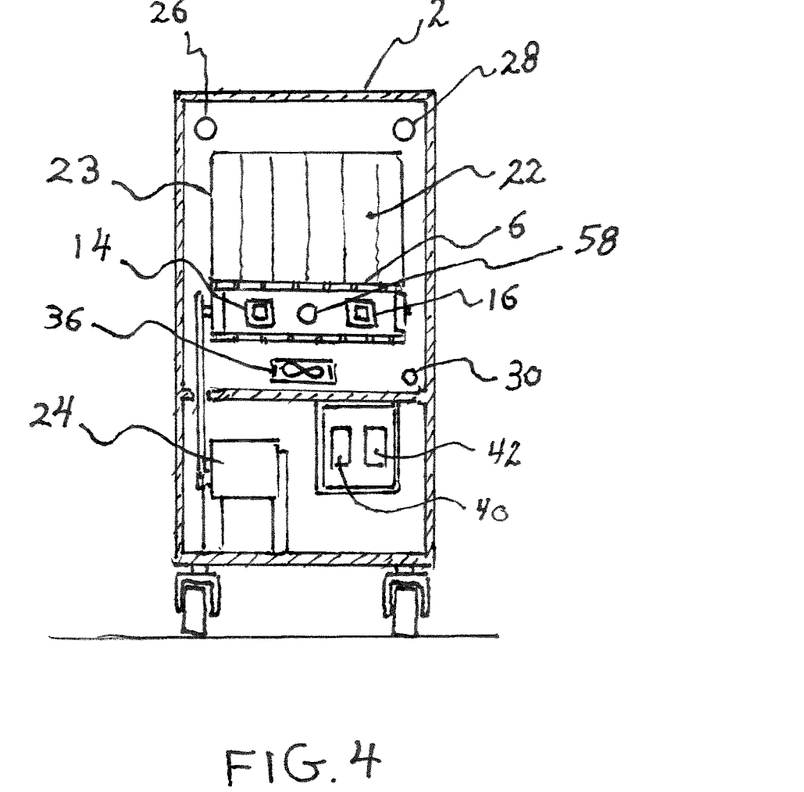
FIG. 4 is a front section view of the present invention taken along line 60 of FIG. 2 showing suitcases on the shelves of the main housing.

Referring back to FIG. 1, toggle switch 11 turns on the heating elements 14, 16 and the UV lights 26, 28, 58 and fan 36 as shown in the front section view in FIG. 4. The heating elements are preferably strip-type fin heaters, each having a heat rating of 750 watts. When the user wishes to have an item of luggage enter the upper housing area 52, the user pushes the "on" button 10, causing the conveyor 6 to turn on. The conveyor 6 automatically turns off when the luggage that has been placed on the conveyor 6 has been drawn into the upper housing area 52. A timing circuit 40 holds the luggage inside the housing for ninety seconds and then re-starts the conveyor 6 to cause the luggage to exit the housing 2 and be placed on a table surface 50 which may include rollers for ease of sliding the luggage off the table 50. The conveyor 6 can be manually turned off by pushing "off" button 8. Emergency switch 12 can be pushed if there is a malfunction in the machine 100, causing the entire machine to turn off.

Figure 2:
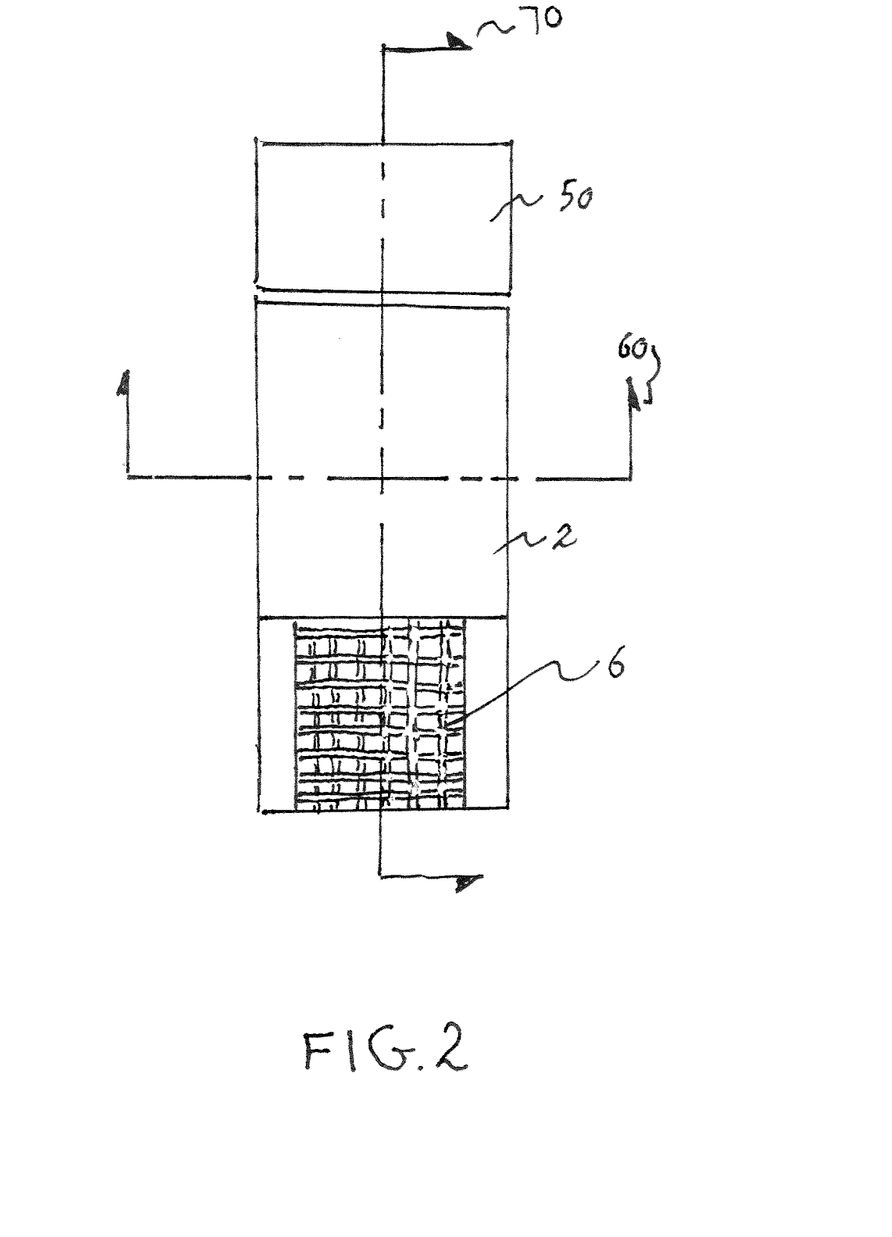
FIG. 2 is a top plan view of the present invention.

FIG. 2 is a top plan view of the system 100. The conveyor 6 is made of open mesh stainless steel links that allow the heat from heaters 14, 16, and light from UV lamp 58 located under a top layer of the conveyor 6, to rise up and evenly heat and illuminate the underside of the luggage, and also to heat the inside of upper housing area 52. An optional fan 36 within housing 2, shown in FIG. 4, can help spread the heat evenly. Temperature sensor 30 shown in FIG. 4 sends heat information to a temperature controller 42 located in the lower housing area 54 which holds the desired temperature of approximately 160 degrees F. to within a tolerance of plus or minus one degree F. The temperature controller 42 is controlled by digital thermostat 56, wherein the temperature sensor 30, temperature controller 42, and thermostat 56 represent a temperature control circuit. The housing 2 includes a top, or upper housing area 52 and a bottom, or lower housing area 54 as shown in the side section view in FIG. 5. The upper housing area 52 is heated by heaters 14, 16, while the lower housing area 54 remains relatively cool. In another embodiment, additional heaters can be used to more quickly heat the luggage and thereby speed up the bug killing process. In this case, four strip heaters can be used. Each strip heater has a one thousand watt capacity. These strip heaters are powered by two hundred and twenty volts AC. In addition, other heat sources may be used, such as vortex heaters and RF heaters.

Figure 3:
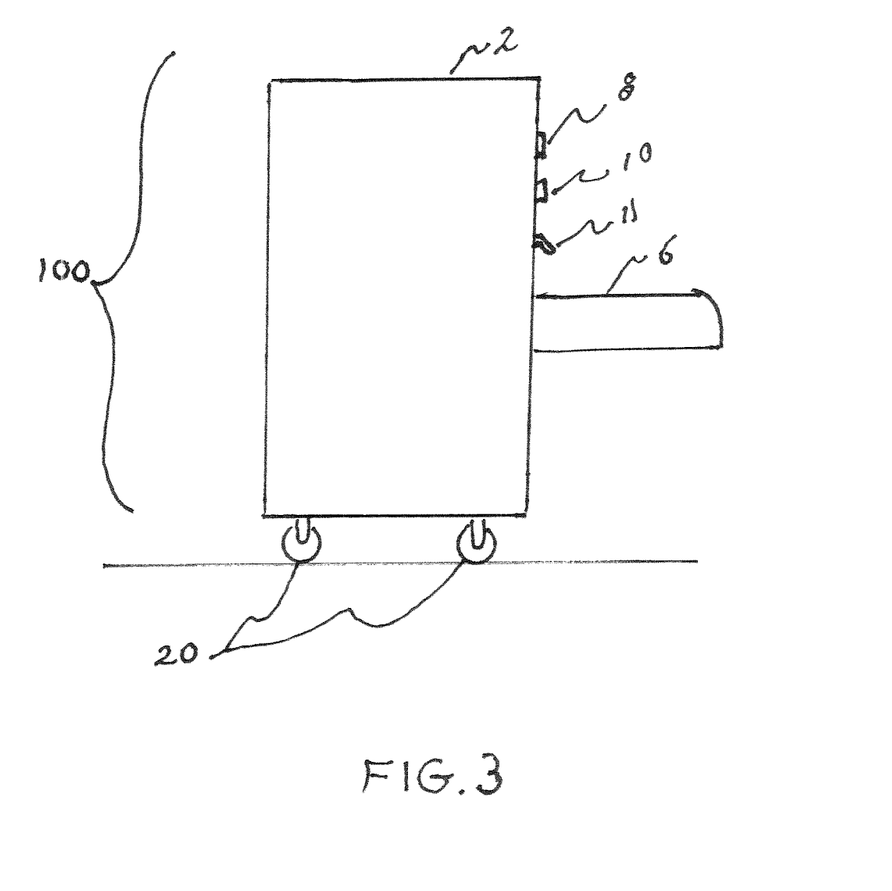
FIG. 3 is a left side view of the present invention.

FIG. 3 is a side view of the system 100. The entire system 100 can be supported by lockable wheels 20.

FIG. 4 is a front section view that vertically bisects the system 100 along the line 60 in FIG. 2. Heater strips 14, 16 and UV lamp 58 can be clearly seen suspended between the top and bottom layers of the conveyor 6. Alternatively, the heaters 14, 16 and lamp 58 can be located underneath the lower level of the conveyor 6 in the area where the fan 36 currently resides. A gear reduced drive motor 24 powers the stainless steel wire mesh conveyor track 6. UV lamps 26, 28 are mounted within the upper housing area 52. A table 50 is at the same height of the top surface of the conveyor 6 allowing a surface for luggage or suitcases to rest after exiting from rear flaps 22.

Figure 5:
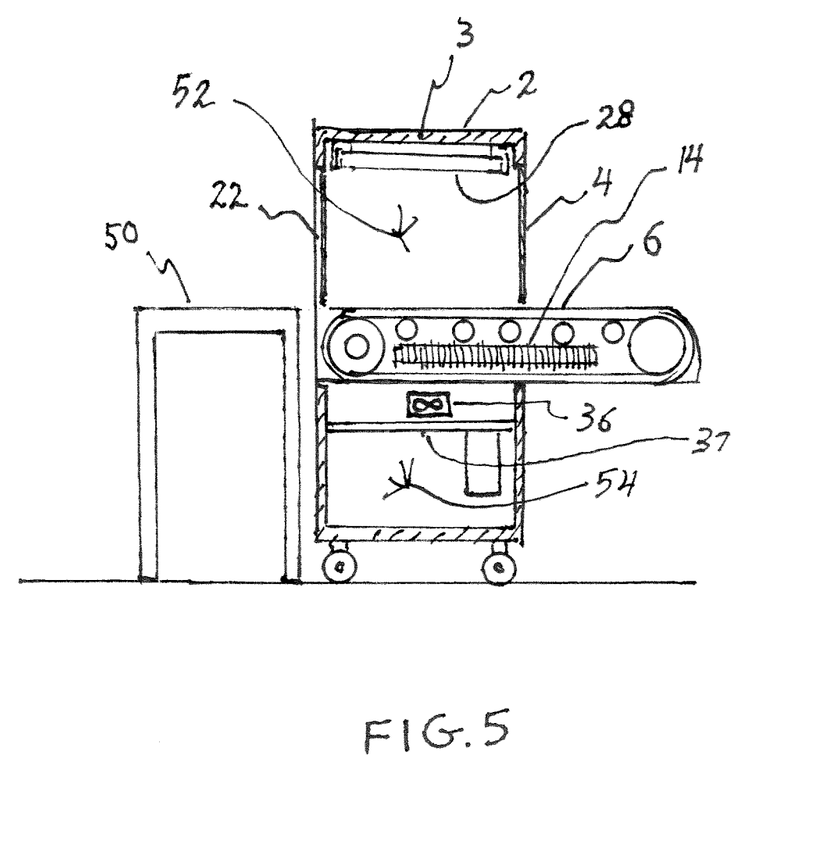
FIG. 5 is a side section view of the present invention taken along line 70 in FIG. 2.

FIG. 5 shows a side section view of the system 100 taken along lines 70 shown in FIG. 2, which clearly shows the placement of heater strips 14, UV lamps 28 and fan 36. The heater strips shown in this embodiment have a power rating of 750 watts each. However, other embodiments can be provided having more heating elements and having greater wattage per element. The housing is made of polished aluminum which helps reflect the UV light to all areas within the housing 2. A special type of aluminum, such as that manufactured by Anomet Inc., can be designed to allow maximum reflectivity of UV light.

The present invention allows users to use a treatment method for killing bedbugs that is free from any Insecticide or Aerosol applications. The combination of heat and the ultraviolent rays control and kill bacteria, viruses, and spores, and aid in the sterilization of the items that pass through the housing 2. Additionally, the system 100 helps eliminate unwanted insects such as flea eggs and all stages of bedbugs.

The easy-to-use portable conveyor can be moved from one location to another with ease. The easy-lock and unlock wheels 20, allows the system to be placed anywhere. As convenient as it is to move from one location to another, the conveyor motor, heating strips, UV lights and fan all operate on 120 VAC and the plug 22 and cord 20 can therefore be plugged into any standard wall socket. This feature makes it readily available for use, rather than to have specially designed 220 electric run to a specific location.

A piece of luggage or bag or other item entering the conveyor 6 will complete the process of killing bed bugs in a matter of 90 seconds. After treatment is completed, the baggage or item has been subject to a germicide treatment which will aid in controlling bacteria, viruses, spores, and in many cases, the sterilization of the exterior of the bag or item. Occasional invaders such as flea eggs or bedbugs have little chance for survival after being subjected to this treatment.

The system 100 is already "Pre-Set" for use. The user simply places his luggage on the conveyor 6 and presses the Start button 8. All the guess work has been taken out, making the experience one that is enjoyable and brings peace-of-mind knowing that unwanted bugs and bacteria have been removed.

Because the process is completed in a matter of 90 seconds, there is no danger to the luggage or item from the heat or exposure to light. The temperature within the unit does not exceed 160 degrees, causing mortality to the insects, but doing no harm to the luggage or item.

The UV lighting is at a controlled amount of exposure within the housing's mirror-like lining. As the lighting reflects off the top, bottom and sides of the unit, it causes a bouncing effect of light-rays in all directions, killing any bacteria, viruses, and spores that it comes in contact with.

The unit is outfitted with an Emergency Stop switch 12 should for any reason the system 100 needs to be stopped prior to completing the cycle.

Figure 6:
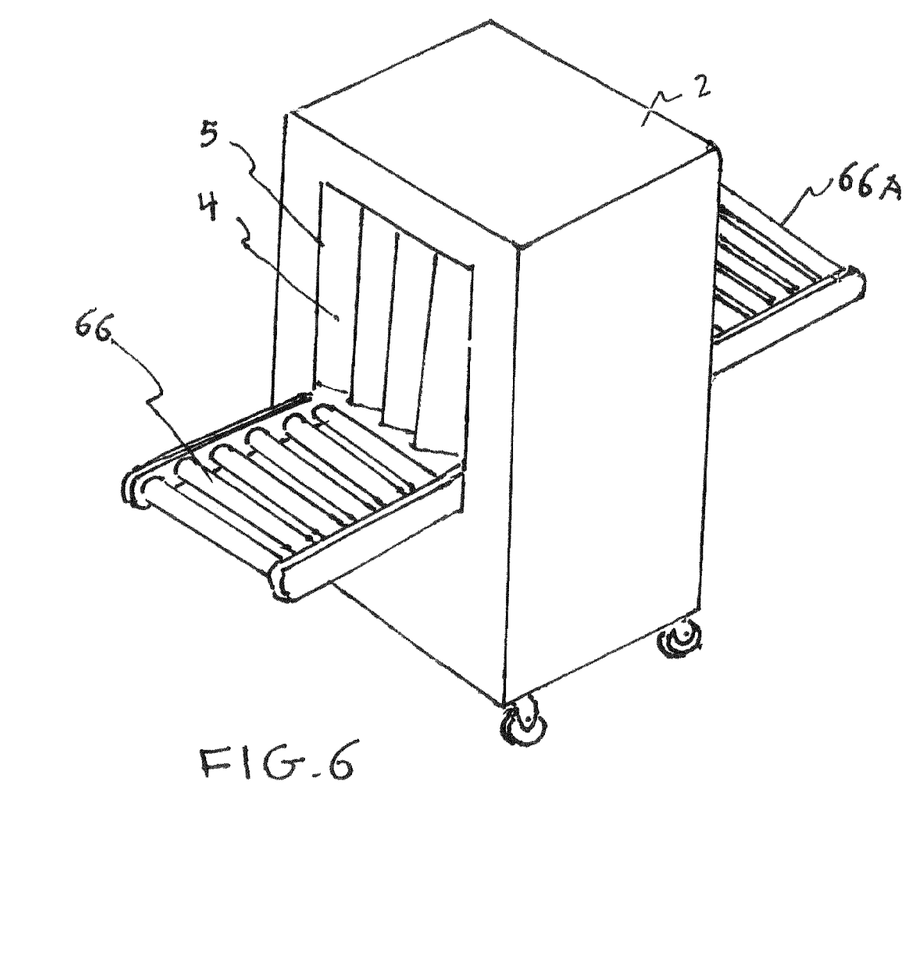
FIG. 6 is a perspective view of an alternate embodiment of the present invention using a roller conveyor.

In an alternate embodiment shown in FIG. 6, a roller type conveyor 66 is used at the entrance point to opening 5 instead of the powered mesh conveyor 6 in the original embodiment. This configuration allows the mesh conveyor 6 to remain inside the heated upper housing interior 52. The item is delivered to an exit conveyor 66A.

We know that in most cases these pests are "hitch-hikers" by nature. Harborage areas for most travelers consist of luggage or suitcase tucks or seams next to pockets or zipper liners. The present invention's nonintrusive method of combining heat and UV rays to the exterior of luggage provides protection without the need for opening personal effects.

The present invention is made to handle everyday use in an average size hotel or motel. However, larger or smaller units can be built and remain within the spirit of the present invention.

While the description above refers to particular embodiments of the present invention, it will be understood that many modifications may be made without departing from the spirit thereof.

What is claimed is:

1. A system for killing bed bugs on an outside surface of an item, comprising:
   a housing divided into an upper housing area and a lower housing area;
   front and rear flap covered apertures located in a front and a rear, respectively, of the upper housing area;
   a horizontally disposed motorized conveyor that is located within the upper housing area;
   at least one heating element located in the upper housing area;
   two or more UV lamps located in the upper housing area;
   a fan located in the upper housing area;
   wherein the at least one heating element, one of the UV lamps, and the fan are located below a top layer of the conveyor; and
   a timing circuit located in the lower housing area, the timing circuit causing the motorized conveyor to draw in one or more items through the front aperture and into the upper housing area, to retain the one or more items within the upper housing area for a predetermined period of time, and then to deliver the one or more items out of the upper housing area via the rear aperture.

2. The system of claim 1, further including:
   a temperature sensor located within the upper housing area and sending information to a temperature controller located in the lower housing area to maintain the temperature within the upper housing area to approximately 160 F degrees;
   a temperature control circuit comprising the temperature sensor, the temperature controller, and a thermostat; and
   a power cord and plug which provides power from a wall socket to the housing.

3. The system of claim 1, wherein the conveyor extends out from the housing by approximately three feet, and is constructed of wire mesh material capable of allowing UV light and heat to strike an underside of an item laying on said conveyor.

4. The system of claim 1, wherein the at least one heating element comprises two 750 watt strip fin type heating elements.

5. The system of claim 1, wherein the at least one heating element includes infrared heating elements, ceramic heating elements, convection heat tubes, vortex heaters, RF heaters or any combination thereof.

6. The system of claim 1, wherein an internal surface of the upper housing area is constructed of sheet metal having a polished finish capable of reflecting UV light rays.

7. The system of claim 1, wherein the at least one heating element acts to bring an internal temperature inside the housing to approximately 160 degrees F. enabling the item to heat up to approximately 120 degrees F. within a ninety second time period.

8. The system of claim 1, wherein the front and rear flap covered apertures are lead lined and allow easy entrance and exit of the item, and further provide a degree of heat retaining insulation.

9. The system of claim 1, wherein the housing is supported on wheels.

10. The system of claim 1, wherein the conveyor is made of rollers.

* * * * *